US00PP29578P2

(12) United States Plant Patent
Dirr et al.

(10) Patent No.: US PP29,578 P2
(45) Date of Patent: Aug. 7, 2018

(54) ***ILEX* PLANT NAMED 'PIIIC-I'**

(50) Latin Name: *Ilex crenata*
Varietal Denomination: PIIIC-I

(71) Applicant: Bailey Nurseries Inc, Newport, MN (US)

(72) Inventors: Michael A. Dirr, Bogart, GA (US); Rhonda Helvick, Madison, GA (US); Oren McBee, Bishop, GA (US); Mark Griffith, Watkinsville, GA (US); Jeff Beasley, Lavonia, GA (US)

(73) Assignee: BAILEY NURSERIES INC., Newport, MN (US)

( * ) Notice: Subject to any disclaimer, the term of this patent is extended or adjusted under 35 U.S.C. 154(b) by 0 days.

(21) Appl. No.: 15/530,605

(22) Filed: Feb. 6, 2017

(51) Int. Cl.
*A01H 5/00* (2018.01)

(52) U.S. Cl.
USPC ..... Plt./247

(58) Field of Classification Search
USPC ..... Plt./247
CPC ..... A01H 5/12; A01H 5/02; A01H 5/00
See application file for complete search history.

(56) References Cited

PUBLICATIONS

Bailey Nurseries First Editions Selected for Success New Varieties 2017/18, retrieved on Mar. 6, 2018, retrieved from the Internet at https://www.baileynurseries.com/media/wysiwyg/bn/our-brands/firsteditions/marketing/brochures/downloads/FE-New_Varieties_2017.pdf, 8 pp. (Year: 2017).*

Griffith Propagation Nursery, Inc. Plant Availability Nov. 3, 2016, retrieved on Mar. 6, 2016, retrieved from the Internet at http://www.griffithnursery.com/Availability_161103.pdf, pp. 1-3. (Year: 2016).*

* cited by examiner

*Primary Examiner* — June Hwu
(74) *Attorney, Agent, or Firm* — Penny J. Aguirre

(57) ABSTRACT

A new cultivar of *Ilex crenata* plant named, 'PIIIC-I', that is characterized by its upright, fastigiate plant habit, its dense, freely branching growth habit, its slightly recurved leaves that are glossy in texture and dark green in color, branches that do not splay or spread apart with age and its lack of fruit production (male flowers).

2 Drawing Sheets

Botanical classification: *Ilex crenata.*
Variety denomination: 'PIIIC-I'.

BACKGROUND OF THE INVENTION

The present invention relates to a new and distinct cultivar of *Ilex crenata* and will be referred to hereafter by its cultivar name, 'PIIIC-I'. 'PIIIC-I' is a new cultivar of holly grown for use as a landscape plant.

The new cultivar of *Ilex* arose from a breeding program conducted by the Inventors in Watkinsville, Ga. 'PIIIC-I' originated as a seedling from seed derived from open pollination of *Ilex crenata* 'Sky Pencil' (not patented). The male parentage is therefore unkown. 'PIIIC-I' was selected as a single unique plant in summer of 2009 from amongst the resulting seedlings.

Asexual propagation of the new cultivar was first accomplished by semi-hardwood stem cuttings by one of the Inventors in Watkinsville, Ga. in 2013. Asexual propagation by semi-hardwood stem cuttings has determined that the characteristics of the new cultivar are stable and are reproduced true to type in successive generations.

SUMMARY OF THE INVENTION

The following traits have been observed repeatedly and represent the characteristics of the new cultivar. These attributes in combination distinguish 'PIIIC-I' as a unique cultivar of *Ilex.*

1. 'PIIIC-I' exhibits an upright, fastigiate plant habit.
2. 'PIIIC-I' exhbits a dense, freely branching growth habit.
3. 'PIIIC-I' exhibits slightly recurved leaves that are glossy in texture and dark green in color.
4. 'PIIIC-I' exhibits branches that do not splay or spread apart with age.
5. 'PIIIC-I' lacks fruit production as it is a male slection.

The female parent, 'Sky Pencil', differs from 'PIIIC-I' in having larger leaves, longer internodes lengths, in producing fruit (female), and in having branches that tend to splay and spread apart. 'PIIIC-I' can be most closely compared to *Ilex* seedlings that also arose from seed planted from open pollination of 'Sky Pencil'; 'SS-04-11' (not patented) and 'SS-01-11' (not patented). 'SS-04-11' differs from 'PIIIC-I' in having larger leaves, longer internodes lengths, a faster growth rate, and branches that tend to flop with age. 'SS-01-11' differs from 'PIIIC-I' in having an oval shaped plant habit, leaves that are smaller in size, a slower growth rate and in producing fruit (female).

BRIEF DESCRIPTION OF THE DRAWINGS

The accompanying colored photographs illustrate the overall appearance and distinct characteristics of a seven-year-old plant of the new cultivar as grown in the ground in Watkinsville, Ga.

The photograph in FIG. 1 provides a side view of the plant habit of 'PIIIC-I'.

Figure 1:
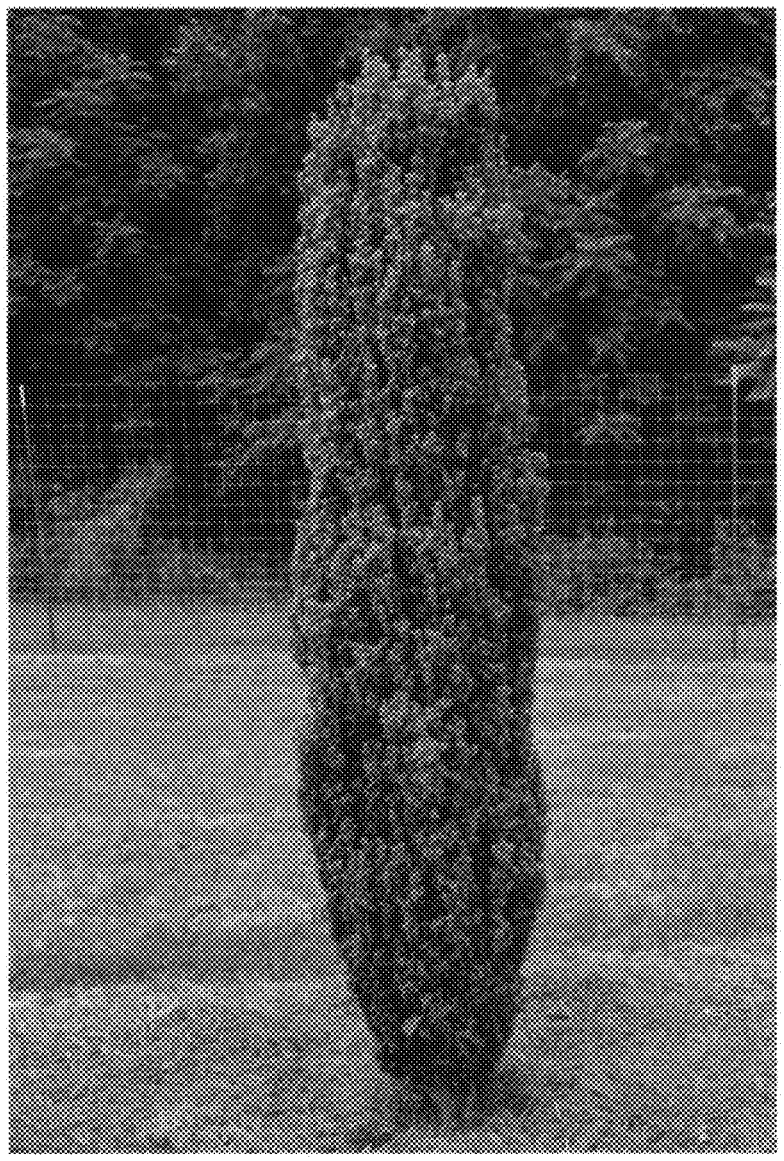
Figure 2:
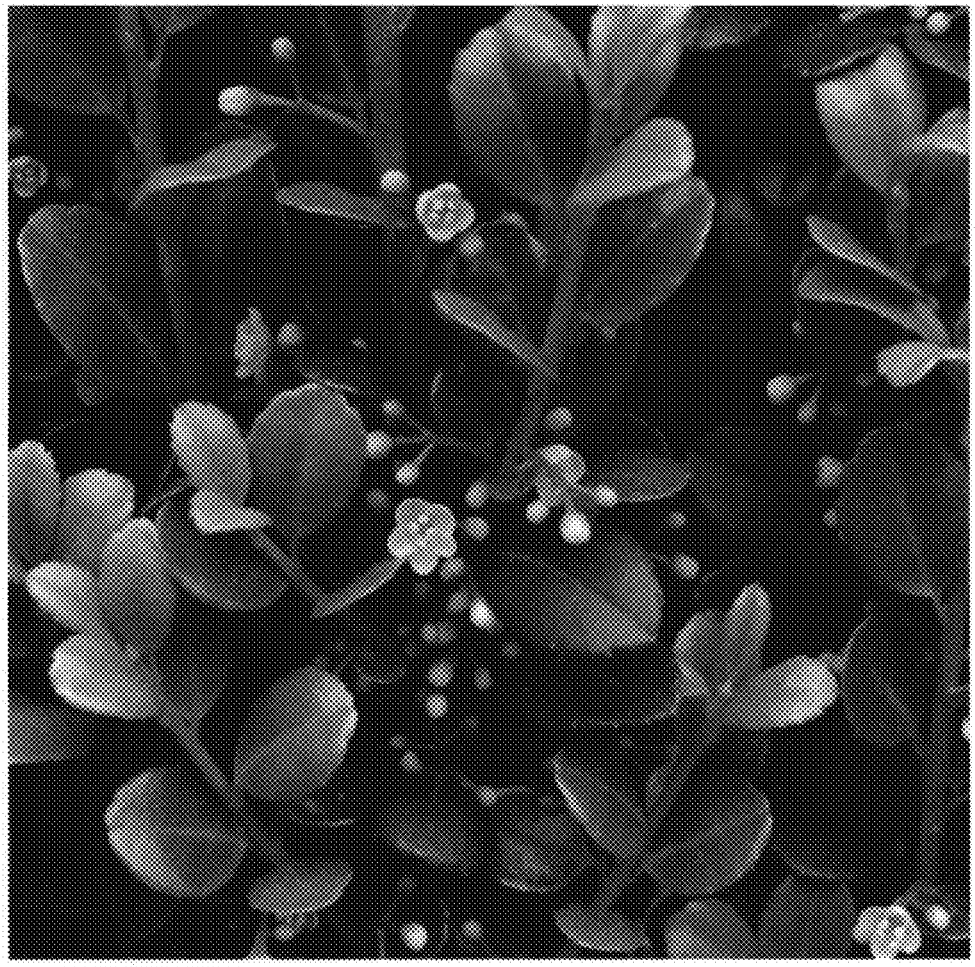

The photograph in FIG. 2 provides a close-up view of the foliage and flowers of 'PIIIC-I'.

The colors in the photographs are as close as possible with the photographic and printing technology utilized and the color values cited in the Detailed Botanical Description accurately describe the colors of the new *Ilex*.

DETAILED BOTANICAL DESCRIPTION

The following is a detailed description of seven-year-old plants as grown in the ground in Watkinsville, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late May to early June in Watkinsville, Ga.

*Plant type.*—Evergreen shrub.

*Plant habit.*—Upright, dense, fastigiate plant habit with numerous lateral branches.

*Height and spread.*—An average of 2 m in height and 50 cm in width for a 7 year-old plant in the landscape.

*Cold hardiness.*—At least in U.S.D.A Zones 6 to 9.

*Diseases resistance.*—No susceptibility or resistance to diseases or pests has been observed.

*Root description.*—Fine, fibrous, freely branched, dense, 156C in color.

*Propagation.*—Semi-hardwood stem cuttings.

*Growth rate.*—Moderate.

*Time required for root development.*—An average of 6 weeks for root initiation in the summer at 32° C., with a rooted plant produced in an average of 4 months.

Branch description:

*Shape.*—Rounded.

*Branch color.*—First year; 144A, 2$^{nd}$ year and older; 196A, mature wood and trunk; 199C.

*Branch size.*—An average of 19 cm in length and 4 mm in diameter (first year 2 mm in length), trunk is an average of 9 cm in diameter at the soil line.

*Branch surface.*—Smooth and glabrous.

*Internode length.*—An average of 7 mm.

*Stem strength.*—Strong.

*Branching.*—Well-branched, dense.

Foliage description:

*Leaf shape.*—Elliptical and slightly recurved.

*Leaf division.*—Simple.

*Leaf base.*—Obtuse.

*Leaf apex.*—Obtuse.

*Leaf fragrance.*—None.

*Leaf venation.*—Pinnate, color; N137A on the upper surface and 138B on the lower surface.

*Leaf margins.*—Entire to slightly crenate with fine apicuate tips on some crenations.

*Leaf arrangement.*—Alternate.

*Leaf aspect.*—Held at a average angle of 30° to the stem (0° vertical).

*Leaf attachment.*—Petiolate.

*Leaf surface.*—Glabrous, glossy, and coriaceous on both surfaces.

*Leaf size.*—An average of 2.4 cm in length and 1 cm in width.

*Leaf quantity.*—An average of 46 per branch 58 cm in length.

*Leaf color.*—Young leaves; upper surface N137A, lower surface 138B, mature leaves; upper surface 147A, lower surface 138B.

*Petioles.*—An average of 5 mm in length and 1 mm in diameter, 146A in color, smooth and glabrous surface.

Flower description:

*Inflorescence type.*—Cymes of campanulate-shaped flowers on axillary nodes of lateral branches.

*Lastingness of inflorescence.*—About 2 weeks.

*Inflorescence size.*—An average of 1 cm in length and 1.5 cm in width.

*Flower fragrance.*—None.

*Flower number.*—An average of 3 per inflorescence.

*Flower aspect.*—Outwards.

*Flower bud.*—Round-oblong in shape, an average of 2 mm in length and 1.5 mm in width, color; N144A.

*Flower form.*—Campanulate.

*Flower size.*—An average of 4.5 mm in width and 2.5 cm in depth.

*Petal.*—An average of 4, ovate in shape, an average of 2 mm in length and width, obtuse apex, rounded base, entire margin, color upper and lower surface 1D, smooth and glabrous on upper and lower surfaces.

*Sepals.*—An average of 4, ovate in shape, an average of 1 mm in length and width, rounded apex, fused based, entire margin, color upper and lower surfaces 144A, smooth and glabrous upper and lower surfaces.

*Peduncles.*—Oval in shape, an average of 6 mm in length and 1 mm in width, held outwards from lateral stems, strong, 145A in color, smooth and glabrous surface.

*Pedicels.*—Rounded in shape, an average of 2 mm in length and 0.5 mm in width, strong, color 145A, smooth and glabrous surface.

Reproductive organs:

*Gynoecium.*—Not present, male flowers only.

*Androecium.*—4 stamens, anthers; basifixed, ovate in shape, about 2 mm in length, and 1A in color, filaments; an average of 3 mm in length and 1D in color, pollen is abundant and 1A in color.

*Seed and fruit.*—Not produced.

It is claimed:

1. A new and distinct cultivar of *Ilex* plant named 'PIIIC-I' as herein illustrated and described.

* * * * *